United States Patent [19]

Morrow

[11] 4,252,806

[45] Feb. 24, 1981

[54] TRIAZOLOQUINOLONES

[75] Inventor: Duane F. Morrow, Evansville, Ind.

[73] Assignee: Mead Johnson & Company, Evansville, Ind.

[21] Appl. No.: 78,535

[22] Filed: Sep. 24, 1979

[51] Int. Cl.$^3$ .............. A61K 31/495; C07D 295/12; C07D 401/14
[52] U.S. Cl. .................................. 424/250; 544/361
[58] Field of Search ............... 544/362, 361; 424/250

[56] References Cited

U.S. PATENT DOCUMENTS 3,381,009   4/1968   Palazzo et al. .................. 544/362

OTHER PUBLICATIONS

Silvestrini et al. Int. J. Neuropharmacol. 7, 587–599 (1968).
Fabre et al. Current Therapeutic Research, 25 (6), 827–834 (1979).

*Primary Examiner*—Jose Tovar
*Attorney, Agent, or Firm*—R. E. Carnahan; R. H. Uloth

[57] ABSTRACT

2-[3-[4-Arylpiperazin-1-yl]propyl]-1,2,4-triazolo[4,3-a]-quinolin-3(2H)-ones are antidepressant agents.

10 Claims, No Drawings

TRIAZOLOQUINOLONES

FIELD OF THE INVENTION

This invention is concerned with heterocyclic carbon compounds of the piperazine series having an additional pyridine ring which is part of a polycyclo ring system (Class 544, Subclass 361). It is also concerned with drug, bio-affecting, and body-treating processes employing these compounds (Class 424, Subclass 250).

DESCRIPTION OF THE PRIOR ART

U.S. Pat. No. 3,381,009 patented Apr. 30, 1968 refers to 1,2,4-triazolo[4,3-a]pyridines which are pyridine analogs of the 1,2,4-triazoio[4,3-a]quinolin-3(2H)-ones of the present invention. The preferred compound of this group of prior art substances is 2-[3-[4-(3-chlorophenyl)-1-piperazinyl]propyl]-1,2,4-triazolo[4,3-a]pyridin-3(2H)-one which is known by the name trazodone, and has also been referred to as AF 1161. Pharmacological data summarized in the foregoing patent reveal that trazodone exhibits tranquilizing action, hypotensive action, and analgesic action in various animal tests. The data resemble that of the major tranquilizers or antipsychotic agents such as chlorpromazine more than the minor tranquilizers or anxiolytic agents such as meprobamate and diazepoxide.

The pharmacological properties of trazodone have been described in more detail by Silvestrini, et al. in International Journal of Neuropharmacology, 7, 587-599 (1968). In clinical use the compound has proven to be an antidepressant equivalent in effectiveness to imipramine but with fewer side effects (Fabre, et al., Current Therapeutic Research, 25, 827-834 (1979)).

SUMMARY OF THE INVENTION

The compounds with which the present invention is concerned have the following structural formula

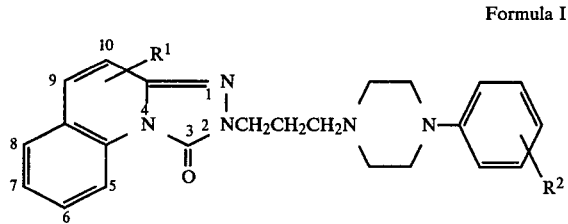

Formula I wherein $R_1$ is hydrogen or lower alkyl having 1 to 4 carbon atoms and $R_2$ is hydrogen, lower alkyl having 1 to 4 carbon atoms, lower alkoxy having 1 to 4 carbon atoms, halogen, or trifluoromethyl. The ring positions are numbered in Formula I for assistance with nomenclature. When $R^1$ is other than hydrogen, it is located in any of the 5-, 6-, 7-, 8-, 9-, or 10- positions of the 1,2,4-triazolo[4,3-a]quinolin-3(2H)-one ring. Similarly, when $R^2$ is one of the substituent groups identified, it may be located in any of the 2-, 3-, or 4-positions of the phenyl ring. The invention includes the pharmaceutically acceptable acid addition salts of the foregoing substances and their use in the treatment of depressive disorders including endogenous depression, neurotic depression, or depression accompanying a psychosis.

The pharmaceutically acceptable acid addition salts are those in which the anion does not contribute significantly to the toxicity or pharmacological activity of the salt and, as such, they are the pharmacological equivalents of the bases of Formula I. They are preferred for medical usage. In some instances, they have physical properties which make them more desirable for pharmaceutical formulation purposes such as solubility, lack of hygroscopicity, compressibility with respect to tablet formation and compatibility with other ingredients with which the substances may be used for pharmaceutical purposes. The salts are made by reaction of the base of Formula I with the selected acid preferably by contact in solution. They may also be made by metathesis or treatment with an ion exchange resin under conditions in which the anion of one salt of the substance of the Formula I is replaced by the anion of another under conditions which allow for separation of the undesired species such as by precipitation from solution or extraction into a solvent, or elution from or retention on an ion exchange resin. Pharmaceutically acceptable acids for the purposes of salt formation of the substances of Formula I include hydrochloric, hydrobromic, hydroiodic, citric, acetic, benzoic, phosphoric, nitric, mucic, isethionic, glucosaccharic, palmitic, heptanoic, and others.

The compounds of the present invention in animal tests are comparable in antidepressant activity to trazodone. Their physical properties are similar but they are substantially less toxic. Accordingly, they may be administered in dosage forms of similar type and size as trazodone with fewer side effects, and less toxic liability. Also, doses two or more times as great as with trazodone may be employed for enhanced effectiveness. They may be safely administered by the oral or parenteral routes in the treatment of depression in doses of from about 150 to 1200 mg. daily.

DETAILED DESCRIPTION OF THE INVENTION

When reserpine is injected intravenously into a mouse at a dose of 2.0 mg./kg., ptosis occurs. However, if the mouse is treated orally with one of the clinically effective antidepressant drugs such as imipramine or trazodone before the reserpine is injected, ptosis is prevented (Niemegeers, Industrial Pharmacology, Vol. 2-Antidepressants, Ed. by S. Fielding and H. Lal, pp. 73-98, Futura, New York, N.Y. 1975). For example, an oral dose of imipramine of 6.5 mg./kg. or of trazodone of 36 mg./kg. will prevent reserpine from having this effect when administered subsequently in 50% of the animals ($ED_{50}$). The present compounds are comparable to trazodone in activity, the substance of Procedure 4 exhibiting an $ED_{50}$ of 29 mg./kg. (per os) and that of Procedure 6 exhibiting an $ED_{50}$ of 27 mg./kg. (per os) in preventing reserpine ptosis in mice.

In groups of 10 mice treated variously with geometrically increasing doses of test compound of from 125 mg./kg. to 2,000 mg./kg., the lethal toxicity ($ALD_{50}$) and the dose at which signs of pharmacologic activity are first evidenced ($ATD_{50}$) can be estimated. For highly active compounds lower doses of the test compound must be employed in order to estimate the $ATD_{50}$. The $ALD_{50}/ATD_{50}$ ratio (mg. per kg. body wt./mg. per kg. body wt.) for the compound of Procedure 4 is 2,000/125-250 and for that of Procedure 6 is >2,000/8-15.7. The ratio for trazodone is 940/2-4. Thus, the present substances have less than one-half the lethal toxicity of trazodone and from less than one-half to one-fiftieth the propensity for producing overt signs of physiological effect ($ATD_{50}$) on oral administration to mice. More particularly, the present substances exert less of a depressant effect on the central nervous system as reflected by less deficit in motor coordination, less interference with normal motor activity, and less analgetic effect than trazodone. Laboratory test data with respect to these properties are arranged below.

|  | ORAL DOSES (mg./kg.) | | |
| --- | --- | --- | --- |
| Test | Formula I $R^1 = H$ $R^2 = 3$-Cl | Formula I $R^1 = 9$-$CH_3$ $R^2 = 3$-Cl | Trazodone |
| Mouse, tail clip (analgetic)[1] | $ED_{50} = 200$ | inactive at 200 | $ED_{50} = 55.5$ |
| Reduction of phenylquinone writhing in mice (analgetic)[2] | $ED_{50} = 40.5$ | $ED_{50} = 51.8$ | $ED_{50} = 21.8$ |
| Reduction of spontaneous motor activity in mice[3] | $AED_{-0.3} = 80$ | inactive at 20, 40, & 80 | $AED_{-0.3} = 15.3$ |
| Rotorod method for motor incordination in mice[4] | inactive at 800 | not tested | $ED_{50} = 44.4$ |
| CNS depression in mice Antagonism of foot shock induced aggression[5] | $ED_{50} = 54$ | $ED_{50} = 36.5$ | $ED_{50} = 22.2$ |
| Inhibition of pernicious preening in mice (anti psychotic or analgetic)[6] | $ED_{50} = 24$ | $ED_{50} = 62$ | $ED_{50} = 43$ |
| Suppression of conditioned avoidance response | inactive at 100 mg/kg | inactive at 100 mg/kg | $ED_{50} = 131.1$ |

[1]Bianchi, et al., Brit. J. of Pharmacology 9, 280 (1954).
[2]Hendershot, et al., J. Pharmcol. & Exptl. Ther. 125, 237 (1959).
[3]Kissel, U.S. Pat. No. 3,100,473 (Aug. 13, 1963).
[4]Kinnaird, et al., J. Pharmacol. & Exptl. Ther. 121, 354 (1957). Cutting, et al., Archives Int. Pharmacodyn. 121, 14 (1959).
[5]Tedeschi, et al., J. Pharmacol. & Exptl. Ther. 125, 28 (1959).
[6]Wilfon, et al., Federation Proceedings 19, 21 (1960).
[7]Albert, et al., Pharmacologist 4, 152 (1962).

The compounds of the present invention are prepared from starting materials of Formulas II and III and the trimethylene dihalide of the formula $XCH_2CH_2CH_2X'$ where X and X' are independently selected from chlorine, bromine, and iodine. Preferably at least one of X and X' is bromine or iodine. $R^1$ and $R^2$ have the same meaning as in Formula I.

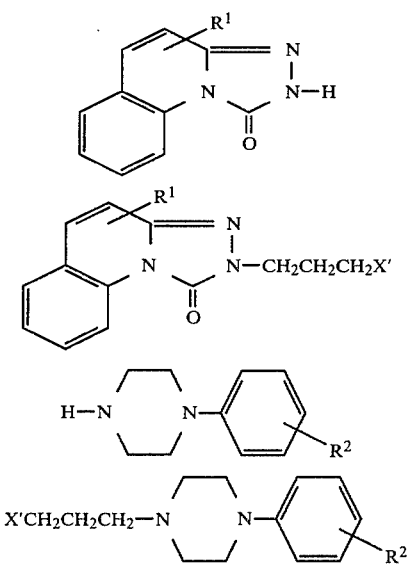

A sequential process is involved in which the starting material of either Formula II or Formula III is caused to react with the dihalide and the resulting intermediate is then caused to react with the other starting material. For instance, the dihalide may be first condensed with the starting material of Formula III and the resulting intermediate then caused to react with the starting material of Formula II. One or the other of the intermediates shown in Formulas IV and V is involved, Formula IV being obtained from Formula II by condensation of the latter with the dihalide and Formula V being obtained from Formula III by condensation of the latter with the dihalide.

In the sequence starting with Formula II the latter is first converted to the sodium or potassium salt by dissolving in warm aqueous sodium or potassium hydroxide and allowing the salt to crystallize from the solution on cooling. The hydrogen atom in the 2-position of Formula II is the acidic functional group which forms the salt. The condensation of the sodium or potassium salt of the starting material of Formula II with the dihalide of the Formula $XCH_2CH_2CH_2X'$ or with the intermediate of Formula V is carried out by heating the two reactants at a temperature in the range of 80°–150° C. in equimolecular quantities in a liquid reaction medium which is inert under the reaction conditions. Preferably, a reaction medium is chosen which has a boiling point within the foregoing temperature range and refluxing of the reaction mixture is employed for temperature control during a reaction period of 2 to 24 hours. Suitable reaction inert liquid media include the liquid hydrocarbons, hydrocarbon nitriles, and hydrocarbon ethers such as xylene, acetonitrile, and dibutylether.

For preparation of the intermediate of Formula V by reaction of the starting material of III with the indicated dihalide, the two reactants are contacted in a reaction inert liquid medium at room temperature for from 2 to 18 hours in the presence of a strong base such as sodium hydroxide or potassium hydroxide when using a reaction medium containing water, or with a sodium or potassium alkoxide, hydride, oxide, or amide when using a liquid medium which is nonreactive to these bases. A mixture of equal volumes in water and acetone is a convenient and preferred reaction medium with sodium hydroxide as the base.

Starting materials of Formula III and the dihalides are articles of commerce or can be prepared by known methods. The triazoloquinolines of Formula II have been described in the literature or can be conveniently prepared by the reaction of 2-chloro-$R^1$-quinoline with semicarbazide. The preferred sequence is to treat the sodium or potassium salt of Formula II with the intermediate of Formula V which is prepared in a preliminary step from the dihalide and the starting material of Formula III. This is illustrated in Procedures 2 and 4 below. Improved yields are obtained according to this sequence relative the sequence involving first preparation of the intermediate of Formula IV, and reaction thereof with Formula III.

DESCRIPTION OF SPECIFIC EMBODIMENTS

In the following procedures temperatures are expressed in degrees Centigrade. Melting points are corrected values according to the USP method where indicated (corr.). The nuclear magnetic resonance (NMR) spectral characteristics refer to chemical shifts downfield ($\delta$) expressed as parts per million (ppm) versus tetramethylsilane as reference standard. The relative area reported for the various shifts corresponds to the number of hydrogen atoms in the individual substituent and the nature of the shift as to multiplicity is reported as broad singlet (bs), singlet (s), multiplet (m), doublet (d), triplet (t), or quadruplet (q) with coupling constant reported where appropriate. The format is NMR (solvent): $\delta$(relative area, multiplicity, J value, and, in some instances, indicated structural characteristics). Abbreviations employed are DMSO-$d_6$ (deuterodimethylsulfoxide), IR (infrared), KBr (potassium bromide), and d (decomposition). Others are common and have well established meanings. The infrared spectra described include only absorption wavelengths (cm$^{-1}$) having functional group identification value. Unless indicated otherwise, KBr was employed as diluent for IR spectral determinations.

PROCEDURE 1.
1,2,4-Triazolo[4,3-a]-quinolin-3(2H)-one

A mixture of 71.9 g. (0.44 mole) of 2-chloroquinoline and 98.22 g. (0.88 mole) of semicarbazide hydrochloride in 150 ml. of 2-ethoxyethanol is heated to reflux and then treated with a solution of 1 ml. of concentrated sulphuric acid (36 N) in 5 ml. of 2-ethoxyethanol. The resulting mixture is refluxed for 18 hrs., cooled to about 60°, and treated with 150 ml. of water. It is then stirred and cooled to 0° and after 0.5 hrs. at 0°, the precipitated solid is collected on a filter to yield 109 g. (59%) of product, m.p. 245°–246°. This material is sufficiently pure to use in the next step.

PROCEDURE 2.
1-(3-Chlorophenyl)-4-(3-chloropropyl)piperazine

To a solution fo 7.36 g. (0.184 mole) of sodium hydroxide in 75 ml. of water and 75 ml. of acetone there is added 17.16 g. (0.074 mole) of 1-(3-chlorophenyl)piperazine hydrochloride and 11.59 g. (0.074 mole) of 1-bromo-3-chloropropane, and the resulting mixture is stirred at 27° for 18 hrs. The organic layer is then separated and concentrated to an oil under reduced pressure. The oil is treated with hot (85°) 6 N HCl until solution is complete, and the resulting solution is filtered and stored at 5° for 18 hrs. The precipitate which forms is collected on a filter to afford 17.52 g. (87%) of the hydrochloride salt of the product, m.p. 198°–200°. Concentration of the mother liquor under reduced pressure and recrystallization of the residue from water affords an additional 1.82 g (9%) of product, m.p. 196°–198°.

PROCEDURE 3. Sodium
1,2,4-Triazolo[4,3-a]quinolin-3(2H)-one

The product of Procedure 1, 57.4 g., (0.31 mole) is dissolved in a solution of 12.19 g. (0.31 mole) of sodium hydroxide in 230 ml. of water at 80°. The solution is then chilled at 5° overnight. A precipitate of the desired sodium salt forms during this period. It is then collected on a filter, and dried at reduced pressure to afford the desired product.

PROCEDURE 4.
2-[3-[4-(3-Chlorophenyl)-1-piperazinyl]propyl]-1,2,4-triazolo[4,3-a]quinolin-3(2H)-one The hydrochloride salt of 1-(3-chloropropyl)-4-(3-chlorophenyl)piperazine, 5.79 g. (0.0187 mole) is dissolved in dilute KOH solution and the free base which is formed is extracted into ether. The ether solution is washed with water and brine, dried over magnesium sulfate, and concentrated under reduced pressure to afford 4.54 g. (88%) of the desired free base. A suspension of 3.45 g. (0.0166 mole) of the sodium salt of 1,2,4-triazolo[4,3-a]quinolin-3(2H)-one and 4.54 g (0.0166 mole) of 1-(3-chloropropyl)-4-(3-chlorophenyl)piperazine in 100 ml. of acetonitrile is treated with approximately 50 mg. of potassium iodide, and refluxed for 24 hrs. The mixture is then cooled and filtered, and the filtrate concentrated to an oil under reduced pressure. The residual oil solidifies when triturated with ether. This solid is recrystallized twice from ethanol to give 4.77 g. (68%) of product, m.p. 99.5°–100.5°.

Anal. Found: C, 65.15; H, 5.86; N, 16.56.

NMR (CDCl$_3$): 2.04 (2,m), 2.54 (6,m), 3.14 (4,m), 4.15 (2,t, 7.0 Hz), 7.10 (9,m), 9.19 (1,m).

IR: 760, 800, 940, 1230, 1460, 1565, 1600, 1715, 2820, and 2940 cm$^{-1}$.

PROCEDURE 5.
9-Methyl-1,2,4-triazolo[4,3-a]quinolin-3(2H)-one

The method of Procedure 1 is repeated with substitution of 2-chloro-4-methylquinoline for the 2-chloroquinoline specified in that procedure in molecularly equivalent amount. The resulting product is recovered in 55% yield, m.p. 280°–281°.

PROCEDURE 6.
2-[3-[4-(3-Chlorophenyl)-1-piperazinyl]propyl]-9-methyl-1,2,4-triazolo[4,3-a]quinolin-3(2H)-one 9-Methyl-1,2,4-triazolo[4,3-a]quinolin-3(2H)-one is substituted in the method of Procedure 3 for the 1,2,4-triazolo[4,3-a]quinolin-3(2H)-one specified in that procedure. The resulting sodium salt is then converted to the desired product according to the method of Procedure 4. in 29% yield after recrystallization from ethanol, m.p. 123°–124° C.

Anal. Found: C, 66.15; H, 6.04; N, 16.15.

NMR (CDCl$_3$): 2.04 (2,m), 2.43 (3,s), 2.54 (6,m), 3.12 (4,m), 4.10 (2,t, 7.0 Hz), 7.26 (8,m), 9.21 (1,m).

IR: 755, 1230, 1460, 1570, 1595, 1635, 1710, 2820, 2940 cm$^{-1}$.

PROCEDURE 7.

1-(3-Chloropropyl)-4-[3-(trifluoromethyl)phenyl]piperazine

The method of Procedure 2 is repeated with substitution of 1-[3-(trifluoromethyl)phenyl]piperazine hydrochloride for the 1-(3-chlorophenyl)piperazine hydrochloride specified in that procedure.

PROCEDURE 8.

2-[3-[4-[3-(Trifluoromethyl)phenyl]-1-piperazinyl]-propyl]-1,2,4-triazolo[4,3-a]quinolin-3(2H)-one Procedure 4 is repeated with substitution of 1-(3-chloropropyl)-4-[3-(trifluoromethyl)phenyl]piperazine for the 1-(3-chloropropyl)-4-(3-chlorophenyl)piperazine specified in that example. The desired product is obtained.

By adaptation of Procedure 1 to various 2-chloro-3,4,5,6,7, or 8- lower alkyl substituted quinoline starting materials, and conversion of the resulting 5,6,7,8,9 or 10-lower alkyl-1,2,4-triazolo[4,3-a]quinolin-3(2H)-ones according to the processes of Procedures 3 and 4, various ring-substituted homologs of the product of Procedure 4 may be prepared as follows.

| Quinoline Starting Material | Formula I $R^2 = 3\text{-}Cl$ |
|---|---|
| 2-Chloro-3-methylquinoline | $R^1 = 10\text{-}CH_3$ |
| 2-Chloro-4-ethylquinoline | $R^1 = 9\text{-}C_2H_5$ |
| 2-Chloro-6-(n-propyl)quinoline | $R^1 = 7\text{-}(n\text{-}C_3H_7)$ |
| 2-Chloro-5-(tert.-butyl)quinoline | $R^1 = 8\text{-}(tert.\text{-}butyl)$ |

Similarly by substitution of other 1-arylpiperazines for 1-(3-chlorophenyl)piperazine in Procedure 2, and conversion of the resulting 1-aryl-4-(3-chloropropyl)-piperazines according to Procedure 4 various other $R^2$-substituted products of Formula I may be prepared as follows.

| Piperazine Starting Material | Formula I $R^1 = H$ |
|---|---|
| 1-phenylpiperazine | $R^2 = H$ |
| 1-(4-methylphenyl)piperazine | $R^2 = 4\text{-}CH_3$ |
| 1-(2-bromophenyl)piperazine | $R^2 = 2\text{-}Br$ |
| 1-(4-fluorophenyl)piperazine | $R^2 = 4\text{-}F$ |
| 1-(3-tert.-butylphenyl)piperazine | $R^2 = 3\text{-}tert.\text{-}C_4H_9$ |
| 1-(4-ethoxyphenyl)piperazine | $R^2 = 4\text{-}C_2H_5O$ |
| 1-[3-(1-methylethoxy)phenyl]piperazine | $R^2 = 3\text{-}OCH(CH_3)_2$ |

For the preparation of pharmaceutical compositions containing the compounds of Formula I in the form of dosage units for oral administration, the compound is mixed with a solid, pulverulent carrier such as lactose, sucrose, sorbitol, mannitol, potato starch, corn starch, amylopectin, cellulose derivatives, or gelatin, as well as with glidents such as magnesium stearate, calcium stearate, polyethylene glycol waxes or the like and compressed into tablets. The tablets may be used uncoated or coated by known techniques.

In the preparation of soft gelatin capsules comprised of a shell made of gelatin and glycerine or the like, the active ingredient is mixed with a vegetable oil and encapsulated in conventional manner. Hard gelatin capsules may contain granules of the active ingredient in combination with a solid, pulverulent carrier such as lactose, sucrose, sorbitol, mannitol, starch (such as e.g. potato starch, corn starch, or amylopectin), cellulose derivatives or gelatin.

Dose units for rectal administration may be prepared in the form of suppositories containing the compound in a mixture with a neutral fat base, or in the form of a gelatin-rectal capsule with a mixture of vegetable oil or paraffin oil.

Liquid preparations suitable for oral administration are suspensions, syrups and elixirs containing from about 0.2% by weight to about 20% by weight of the active ingredient.

A suitable injectible composition comprises an aqueous solution of a water soluble pharmaceutically acceptable salt adjusted to physiologically acceptable pH.

What is claimed is:

1. A 2-substituted-1,2,4-triazolo[4,3-a]quinolin-3(2H)-one having the formula

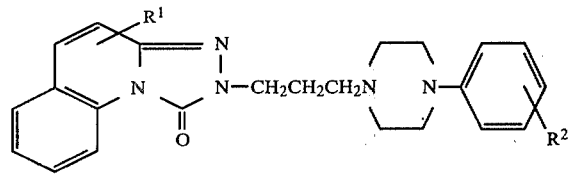

wherein $R^1$ is hydrogen or lower alkyl located in the 5-, 6-, 7-, 8-, 9-, or 10-position of the 1,2,4-triazolo[4,3-a]quinolin-3(2H)-one ring and having 1 to 4 carbon atoms, and $R^2$ is hydrogen, or a substituent attached to the 2-, 3-, or 4- position of the phenyl ring and selected from lower alkyl having 1 to 4 carbon atoms, lower alkoxy having 1 to 4 carbon atoms, halogen, or trifluoromethyl, or a pharmaceutically acceptable acid addition salt thereof.

2. The compound of claim 1 wherein $R^1$ is hydrogen and $R^2$ is chlorine.

3. The compound of claim 1, 2-[3-[4-(3-chlorophenyl)-1-piperazinyl]propyl]-1,2,4-triazolo[4,3-a]-quinoline-3(2H)-one.

4. The compound of claim 1 wherein $R^1$ is lower alkyl having 1 to 4 carbon atoms and $R^2$ is chlorine.

5. The compound of claim 4 wherein $R^1$ is located in the 5-, 6-, 7-, or 8- position.

6. The compound of claim 4 wherein $R^1$ is located in the 9- or 10- position.

7. The compound of claim 1, 2-[3-[4-(3-chlorophenyl)-1-piperazinyl]propyl]-9-methyl-1,2,4-triazolo[4,3-a]-quinoline-1(2H)-one.

8. The compound of claim 1 wherein $R^1$ is hydrogen and $R^2$ is trifluoromethyl.

9. The compound of claim 1, 2-[3-[4-[3-(trifluoromethyl)phenyl]-1-piperazinyl]propyl]-1,2,4-triazolo[4,3-a]-quinoline-3(2H)-one.

10. The process for exerting an anti-depressant effect which comprises administering orally or parenterally to a patient suffering from either neurotic or endogenous depression a non-toxic anti-depressively effective dose of a compound claimed in claim 1.

* * * * *